United States Patent
Kataoka et al.

(10) Patent No.: US 7,102,025 B2
(45) Date of Patent: Sep. 5, 2006

(54) METHOD FOR PRODUCING ALKYL AND/OR CYCLOALKYL-SUBSTITUTED CYCLIC NITRILE

(75) Inventors: Kentaro Kataoka, Niigata (JP); Yoshikazu Shima, Niigata (JP); Kenji Inamasa, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 51 days.

(21) Appl. No.: 10/951,592

(22) Filed: Sep. 29, 2004

(65) Prior Publication Data

US 2005/0124823 A1 Jun. 9, 2005

(30) Foreign Application Priority Data

Sep. 29, 2003 (JP) .............................. 2003-337290

(51) Int. Cl.
*C07C 253/28* (2006.01)
*C07B 43/08* (2006.01)

(52) U.S. Cl. ...................................................... 558/315

(58) Field of Classification Search ................ 558/315
See application file for complete search history.

(56) References Cited

FOREIGN PATENT DOCUMENTS

| DE | 19647795 | 5/1998 |
| EP | 1136120 | 9/2001 |
| WO | WO 96/36593 | * 11/1996 |

* cited by examiner

*Primary Examiner*—Fiona T. Powers
(74) *Attorney, Agent, or Firm*—Antonelli, Terry, Stout and Kraus, LLP.

(57) ABSTRACT

In the production method of the invention, a cyclic aldehyde having an alkyl group and/or a cycloalkyl group directly bonded to a skeletal ring and a formyl group directly bonded to the skeletal ring is brought into contact with ammonia and oxygen in vapor phase in the presence of a catalyst. As a result thereof, the formyl group is selectively ammoxidized into a cyano group to convert the cyclic aldehyde into a corresponding cyclic nitrile. The method enables a long-term, high-yield production of the cyclic nitrile using a reduced amount of ammonia.

10 Claims, No Drawings

METHOD FOR PRODUCING ALKYL AND/OR CYCLOALKYL-SUBSTITUTED CYCLIC NITRILE

BACKGROUND OF THE INVENTION

1. Field of the Invention

The present invention relates to a method for producing an alkyl and/or cycloalkyl-substituted cyclic nitrile by the reaction of a corresponding cyclic aldehyde having a substituent such as alkyl group and cycloalkyl group with ammonia and oxygen.

2. Description of the Prior Art

Various methods have been known for the production of aromatic nitrites by the reaction of aromatic aldehydes and ammonia. For example, proposed are a method in which 20 mol of ammonia per one mole of an aromatic aldehyde is subjected to a vapor-phase catalytic reaction in the presence of a supported catalyst of copper on alumina, and then subjected to the dehydrogenation reaction into an aromatic nitrile (J. Org. Chem., 1981, 46, 754–757), a method in which an aromatic nitrile is produced by a vapor-phase catalytic reaction of an aromatic aldehyde and ammonia in the presence of a catalyst containing copper oxide and at least one of zinc oxide and chromium oxide (JP 2002-179636A), and a method in which an aromatic nitrile is produced by a vapor-phase catalytic reaction of 14 to 50 mol of ammonia per one mole of an aromatic aldehyde in the presence of molybdenum nitride (DE 19518398A). However, since a large excessive amount of ammonia should be used in these methods, the use of these methods in industrial scale involves problems of increased costs for recovery of ammonia. As another problem, it has been pointed out that the yield is reduced by the by-production of high-boiling compounds in the proposed methods (JP 2000-239247A).

If the high-boiling compounds accumulate on catalyst beds, the pressure difference of the catalyst beds increases and the catalytic activity is reduced. Therefore, the catalyst should be regenerated by removing the accumulated high-boiling compounds at regular intervals. However, it is difficult in the above methods to regenerate and reuse the catalyst by removing the high-boiling compounds accumulated on catalyst beds in a economically advantageous manner, because the copper catalyst is used in reductive atmosphere. For example, the regeneration of a deactivated catalyst by calcination in the presence of oxygen is not suitable for the above methods because the catalyst itself is oxidized.

Another method for producing the aromatic nitrile is the ammoxidation of an aromatic aldehyde in the presence of ammonia and oxygen. For example, the aromatic nitrile is produced by reacting an aromatic aldehyde with oxygen in a methanol solution containing ammonia and sodium methylate in the presence of copper chloride catalyst (Rec. Trav. Chim., 1963, 82, 757–765). However, this method requires expensive materials because the catalyst solution is highly corrosive, and increases the cost for recovering the solvent because a large amount of solvent is used.

It has been also known to produce benzonitrile by the ammoxidation of benzaldehyde in which benzaldehyde is brought into contact with ammonia and oxygen in vapor phase in the presence of a catalyst. Kogyo Kagaku Zasshi, 1964, 67, 1542–1545 teaches that the ammoxidation of benzaldehyde with ammonia and oxygen in the presence of a vanadium oxide-aluminum oxide catalyst provides benzonitrile in 85% yield. However, this document describes nothing about the reaction of an aromatic aldehyde having a substituent such as alkyl group into a corresponding aromatic nitrile.

SUMMARY OF THE INVENTION

As mentioned above, it is difficult to stably produce a cyclic nitrile from a corresponding cyclic aldehyde having a substituent such as alkyl group by known methods in a high yield with low costs. Accordingly, an object of the present invention is to provide a method for producing an alkyl and/or cycloalkyl-substituted cyclic nitrile by the reaction of a corresponding cyclic aldehyde having a substituent such as alkyl group and cycloalkyl group with ammonia and oxygen, which is capable of reducing the amount of ammonia to be used and producing the cyclic nitrile in high yields for a long period of time.

As a result of extensive research for solving the above problems, the inventors have found that the alkyl and/or cycloalkyl-substituted cyclic nitrile is produced in high yields using ammonia in an amount smaller than used in the conventional methods without oxidizing the substituent by reacting a corresponding cyclic aldehyde having a substituent such as alkyl group and cycloalkyl group with ammonia and oxygen under specific conditions in the presence of a catalyst. The inventors have further found that the deactivated catalyst is regenerated by a simple method to eliminate the increased pressure difference of a catalyst bed due to the formation of high-boiling compounds.

Thus, the present invention relates to a method for producing an alkyl and/or cycloalkyl-substituted cyclic nitrile, which comprises a step of bringing a cyclic aldehyde having an alkyl group and/or a cycloalkyl group directly bonded to a skeletal ring and a formyl group directly bonded to the skeletal ring into contact with ammonia and oxygen in vapor phase in the presence of a catalyst to selectively ammoxidizing the formyl group into a cyano group, wherein the catalyst contains at least one oxide selected from the group consisting of oxides of V, Mo and Fe; wherein the cyclic aldehyde is brought into contact with ammonia in an amount of 1 to 20 in terms of an equivalent ratio, ammonia/formyl group, with respect to the formyl group of the cyclic aldehyde; and wherein the cyclic aldehyde is brought into contact with oxygen in an amount of 0.4 to 50.0 in terms of an equivalent ratio, $(O_2 \times 2)$/formyl group, with respect to the formyl group of the cyclic aldehyde.

According to the present invention, by reacting an alkyl and/or cycloalkyl-substituted cyclic aldehyde with ammonia and oxygen in the presence of a catalyst, an alkyl and/or cycloalkyl-substituted cyclic nitrile is produced in high yields. The deactivated catalyst is regenerated by a simple method, thereby making it possible to eliminate the increased pressure difference of a catalyst bed caused by the formation of high-boiling compounds. The present invention enables the production of the alkyl and/or cycloalkyl-substituted cyclic nitrile from the alkyl and/or cycloalkyl-substituted cyclic aldehyde in an industrially advantageous manner.

DETAILED DESCRIPTION OF THE INVENTION

The starting compound used in the present invention is a cyclic aldehyde having a substituent R (hereinafter referred to as "substituted cyclic aldehyde"), i.e., a cyclic compound having at least one substituent R and at least one formyl group, each directly bonded to the skeletal ring.

The substituent R is an alkyl group, preferably an alkyl group having 1 to 6 carbon atoms, such as methyl, ethyl, n-propyl, isopropyl, n-butyl, isobutyl, sec-butyl, tert-butyl, n-pentyl, isopentyl, neopentyl, n-hexyl, isohexyl and neohexyl; or a cycloalkyl group, preferably a cycloalkyl group having 4 to 6 carbon atoms, such as cyclobutyl, cyclopentyl and cyclohexyl. Two or more R groups, if present, may be the same or different. The substituted cyclic aldehyde may further have at least one substituent Y inert to the reaction such as phenyl, hydroxyl, alkoxyl groups such as methoxy and ethoxy, halogen such as fluorine, chlorine, bromine and iodine, amino and nitro, each directly bonded to the ring. Two or more Y groups, if present, may be the same or different.

The skeletal ring of the substituted cyclic aldehyde may be a carbon monocyclic ring such as cyclopentadiene, benzene, cyclohexadiene, cyclohexene and cyclohexane; a carbon polycyclic ring such as biphenyl; a fused carbon ring such as naphthalene, dihydronaphthalene, tetralin, decalin, pentalene, anthracene, phenanthrene, biphenylene, fluorene and acenaphthylene; a nitrogen-containing five-membered ring such as pyrrole, pyrroline, pyrrolidine, pyrazole, imidazole, imidazoline, imidazolidine, oxazole, isooxazole, thiazole and isothiazole; a nitrogen-containing six-membered ring such as pyridine, piperidine, pyridazine, pyrimidine, pyrazine, piperazine and triazine; a nitrogen-containing bicyclic fused ring such as pyrrolizine, pyrindine, indolizine, indole, isoindole, indazole, benzimidazole, quinoline, isoquinoline, quinolizine, cinnoline, quinazoline, quinoxaline, phthalazine, naphthyridine, benzoxazole, indoxazene, anthranil, benzothiazole and benzoisothiazole; a nitrogen-containing tricyclic fused ring such as carbazole, phenanthridine, phenanthroline, acridine, acridan, phenazine, phenothiazine and phenoxazine; an oxygen-containing ring such as furan, pyran, benzofuran, isobenzofuran, chromene, isochromene, xanthene and oxanthrene; or a sulfur-containing ring such as thiophene, thiopyran, benzothiophene, thiochromene, isothiochromene, thioxanthen, thianthrene and phenoxathiin.

The substituted cyclic aldehydes include various compounds derived from any combinations of the above ring structure and the substituent or substituents. Examples thereof having a skeletal benzene ring include o-tolualdehyde, m-tolualdehyde, p-tolualdehyde, 2,4-dimethylbenzaldehyde, 2,6-dimethylbenzaldehyde, 3,4-dimethylbenzaldehyde, 2,4,5-trimethylbenzaldehyde, 2,4,6-trimethylbenzaldehyde, 4-ethylbenzaldehyde, 4-isopropylbenzaldehyde and 4-isobutylbenzaldehyde. The substituted cyclic aldehydes and the position(s) of the substituent(s) are not limited to those mentioned above. The substituted cyclic aldehydes may be used alone or in combination.

In the present invention, a commercially available ammonia may be used as the starting material without any limitation. The amount of ammonia to be used is one (theoretical amount) or more in terms of an equivalent ratio (ammonia/formyl group) with respect to the formyl group in the substituted cyclic aldehyde. Higher the equivalent ratio of the ammonia to the formyl group, more advantageous for the yield of the alkyl and/or cycloalkyl-substituted cyclic nitrile (hereinafter referred to as "substituted cyclic nitrile"). However in view of the recovery costs of non-reacted ammonia, the equivalent ratio is 1 to 20, preferably 1 to 10, and more preferably 2 to 5.

The oxygen source used in the present invention is usually air. The amount of oxygen to be fed is 0.4 to 50.0, preferably 0.4 to 10.0, more preferably 0.8 to 4.0 in terms of an equivalent ratio, $(O_2 \times 2)$/formyl group, with respect to the formyl group of the substituted cyclic aldehyde. If less than 0.4, the conversion of the substituted cyclic aldehyde is unfavorably low. If higher than 4.0, the yield of the substituted cyclic nitrile is lowered because of side reactions.

The reaction of the substituted cyclic aldehyde with ammonia and oxygen is carried out in vapor phase in the presence of a catalyst. The reaction manner may be either batch wise, semi-batch wise or continuous, with the continuous manner being industrially preferred. The continuous manner may be conducted in either fixed bed, fluidized bed or moving bed method.

The substituted cyclic aldehyde is preferably mixed with ammonia and oxygen in the presence of a catalyst after separately fed into a reactor rather than in the absence of a catalyst. If the substituted cyclic aldehyde is mixed with ammonia and oxygen in the absence of the catalyst and then fed into a catalyst bed, high-boiling compounds are by-produced to increase the pressure difference of the catalyst bed and reduce the yield of the substituted cyclic nitrile.

In the vapor-phase reaction, the starting substituted cyclic aldehyde and a mixture of ammonia and oxygen are preferably fed into a catalyst bed after converted into gases, although not limited thereto. The starting substituted cyclic aldehyde may be fed after diluted with a diluent such as solvent and inert gas. Examples of the diluent inert gas include nitrogen, argon and helium, with nitrogen being preferred in view of costs. As the diluent solvent, preferred are compounds having no functional group reactive with oxygen and ammonia, for example, benzene.

The reaction is carried out in the presence of a catalyst. Preferred are catalysts containing at least one oxide selected from the group consisting of oxides of V, Mo and Fe (first metals). Catalysts containing oxide of V are particularly preferred. More preferred are catalysts further containing at least one oxide selected from the group consisting of oxides of Mg, Ca, Ba, La, Ti, Zr, Cr, W, Mn, Co, Ni, B, Al, Ge, Sn, Pb, P, Sb and Bi (second metals). In case the catalyst contains the oxide of two or more kinds of metal, examples of the combination of metals include following systems, V—Cr, V—Sb, V—Sn, V—Co, V—Ni, V—P, V—Mn, V—Mo, Mo—Bi, Mo—Sn, Mo—P, Fe—Sb, and Fe—P. Based upon these systems, the catalyst may further contain one or more metal elements mentioned above(the first and/or second metals). Still more preferred are catalysts further containing an alkali metal. When the catalyst further contains at least one oxide of second metal, the atomic ratio of the first metal or metals and the second metal or metals in the catalyst is preferably 1:0.01 to 10, more preferably 1:0.01 to 5. When the catalyst further contains an alkali metal, the atomic ratio of the first metal or metals and the alkali metal or metals in the catalyst is preferably 1:0.001 to 0.5, more preferably 1:0.001 to 0.2.

The catalyst can be used as it is without using a carrier. The catalyst may be supported on known carrier such as silica, alumina, silica-alumina, titania, silica-titania, zirconia, silicon carbide, etc. and preferably silica. The amount of the carrier used is preferably 20 to 95%, more preferably 40 to 95% by weight of the total weight of the catalyst.

For example, a catalyst comprising vanadium oxide, chromium oxide, boron oxide, alkali metal oxide and a heteropolyacid as disclosed in JP 11-246504A brings about excellent results in conducting the production method of the invention. If the catalytic activity is lowered after a long term reaction, this type of catalyst can be easily regenerated by calcination in the presence of oxygen. Simultaneously, the high-boiling compounds accumulated on the catalyst bed are decomposed and removed, eliminating the increased pressure difference of the catalyst bed.

The present invention will be described on the reaction using a reactor of vapor flow type. The temperature of the reaction of the substituted cyclic aldehyde between ammonia and oxygen is preferably 200 to 450° C., more preferably 250 to 400° C. If less than 200° C., the conversion of the substituted cyclic aldehyde is low. If higher than 450° C., the yield of the substituted cyclic nitrile is reduced because of the side reactions. WHSV (feeding amount by weight of the substituted cyclic aldehyde per unit weight of catalyst and per one hour) is preferably 0.005 to 5 h$^{-1}$, more preferably 0.01 to 1 h$^{-1}$. An excessively small WHSV is not economical because a large size of reactor is required. When WHSV is too large, the conversion of the substituted cyclic aldehyde is lowered. SV (space velocity of a mixed gas comprising the substituted cyclic aldehyde, ammonia, air and an optional diluent) is preferably 1 to 100000 h$^{-1}$, more preferably 10 to 10000 h$^{-1}$. An excessively small SV is not economical because a large size of reactor is required. When SV is too large, the conversion of the substituted cyclic aldehyde is lowered. The reaction may be carried out under atmospheric pressure, under reduced pressure or under pressure, preferably 0 to 0.4 MPaG.

The deactivated catalyst after a long term reaction is regenerated by the calcination in the presence of oxygen to recover its activity. Since the high-boiling compounds accumulated on the catalyst bed are also decomposed and removed by the calcination, the increased pressure difference of the catalyst bed is eliminated. The oxygen source for the regeneration of catalyst is generally air which may be diluted by a diluent such as inert gas. The oxygen concentration in the calcination atmosphere is preferably 1 to 21% by volume. Examples of the inert gas for use as the diluent include nitrogen, argon and helium, with nitrogen being preferred in view of production economy. The temperature for regenerating the catalyst is preferably 300 to 700° C., more preferably 350 to 650° C. If lower than 300° C., a long term is required for the regeneration and the high-boiling compounds accumulated on the catalyst are not completely removed by decomposition. If higher than 700° C., the cost for heating is increased to make the production economy poor.

The regeneration of catalyst is carried out in the reactor for ammoxidation with the catalyst being held in the reactor by discontinuing the feeding of the starting substituted cyclic aldehyde and ammonia and then calcining the catalyst while feeding only a heated air which is optionally diluted with a diluent. Alternatively, the catalyst taken out of the reactor is regenerated by calcination and then returned to the rector.

By the reaction described above, the formyl group in the starting substituted cyclic aldehyde is selectively ammoxidized into cyano group to produce the substituted cyclic nitrile in high yields. For example, from the substituted cyclic aldehydes having a skeletal benzene ring such as o-tolualdehyde, m-tolualdehyde, p-tolualdehyde, 2,4-dimethylbenzaldehyde, 2,6-dimethylbenzaldehyde, 3,4-dimethylbenzaldehyde, 2,4,5-trimethylbenzaldehyde, 2,4,6-trimethylbenzaldehyde, 4-ethylbenzaldehyde, 4-isopropylbenzaldehyde and 4-isobutylbenzaldehyde, respectively produced are o-tolunitrile, m-tolunitrile, p-tolunitrile, 2,4-dimethylbenzonitrile, 2,6-dimethylbenzonitrile, 3,4-dimethylbenzonitrile, 2,4,5-trimethylbenzonitrile, 2,4,6-trimethylbenzonitrile, 4-ethylbenzonitrile, 4-isopropylbenzonitrile and 4-isobutylbenzonitrile. The conversion of the alkyl group and/or the cycloalkyl group in the starting substituted cyclic aldehyde is extremely low, and the ratio of the alkyl group or the cycloalkyl group remained not converted by the reaction is generally 90 mol % or higher.

The substituted cyclic nitrile thus produced is collected by a known method, for example, a method of cooling the reaction product mixture to a temperature sufficiently low for precipitating the product or a method of washing the reaction product gas with an appropriate solvent such as water. Thereafter, the substituted cyclic nitrile is isolated by a combination of known unit operations such as concentration and distillation.

The present invention is described in more detail with reference to the following examples. However, it should be noted that the scope of the present invention is not limited thereto. The conversion, yield and selectivity referred to in the examples were calculated from the following equations.

Conversion (mol %)=Substituted cyclic aldehyde reacted (mol)×100/Substituted cyclic aldehyde fed (mol)

Yield (mol %)=Substituted cyclic nitrile produced (mol)×100/Substituted cyclic aldehyde fed (mol)

Selectivity (mol %)=Substituted cyclic nitrile produced (mol)×100/Substituted cyclic aldehyde reacted (mol)

REFERENCE EXAMPLE

Preparation of Catalyst

Into a mixture of 229 g of vanadium pentoxide ($V_2O_5$) and 500 mL of water heated to 80 to 90° C., 477 g of oxalic acid was dissolved under thorough stirring to obtain a vanadyl oxalate solution. Separately, into a mixture of 963 g of oxalic acid and 400 mL of water heated to 50 to 60° C., a solution of 252 g of chromic anhydride ($CrO_3$) in 200 mL of water was added under thorough stirring to prepare a chromium oxalate solution. The vanadyl oxalate solution and the chromium oxalate solution were mixed at 50 to 60° C. to prepare a vanadium-chromium solution, to which a solution of 41.1 g of phosphomolybdic acid ($H_3[PMo_{12}O_{40}]$ $.20H_2O$) in 100 mL of water and a solution of 4.0 g of potassium acetate ($CH_3COOK$) in 100 mL of water were successively added. Then, 2500 g of a 20 wt % aqueous silica sol ($Na_2O$ content: 0.02% by weight) was added to the resultant mixture. The obtained slurry was added with 78 g of boric acid ($H_3BO_3$) under thorough stirring and then concentrated by heating until the amount of the slurry was reduced to about 3800 g. The resultant catalyst solution was spray-dried while keeping the inlet temperature at 250° C. and the outlet temperature at 130° C. The catalyst thus spray-dried was dried for 12 h in a dryer at 130° C., pre-calcined at 400° C. for 0.5 h, and then calcined at 550° C. for 8 h under air flow to obtain a final product of catalyst. The content of the alkali metal was 0.21% by weight, the atomic ratio of V:Cr:B:Mo:P:Na:K was 1:1:0.5:0.086:0.007:0.009:0.020, and the catalyst concentration was 50% by weight.

EXAMPLE 1

Into a reaction tube having an inner diameter of 23 mmφ, 40 mL (42 g) of the catalyst obtained in Reference Example was packed. The temperature of the catalyst bed was raised to 320° C. (reaction temperature). A benzene solution containing 25% by weight of p-tolualdehyde and nitrogen were introduced into an evaporating tube that had been heated to 320° C., evaporated and mixed there, and fed into the catalyst bed from its bottom. Simultaneously, ammonia and air that had been heated to 320° C. were fed into the catalyst bed at the position 5 mm above its bottom to allow the fluidized catalytic reaction of the reactants to proceed. The chemical composition of the mixed gas fed into the catalyst bed during the reaction was p-tolualdehyde:benzene:ammonia oxygen:nitrogen=1.0:4.8:3.0:0.56:90.6 in terms of percent by volume. WHSV was 0.027 $h^{-1}$, and SV was 528 $h^{-1}$. After 2.0 h from the initiation of the reaction, the reaction product gas flowing out of the top of the reaction tube was analyzed. The conversion of p-tolualdehyde was 99.1 mol %, the yield of p-tolunitrile was 93.4 mol %, and the selectivity was 94.3 mol %. The yield of by-produced terephthalonitrile was 4.1 mol %.

EXAMPLE 2

The procedure of Example 1 was repeated except for increasing the feeding amount of ammonia. The chemical composition of the mixed gas fed into the catalyst bed during the reaction was p-tolualdehyde:benzene:ammonia:oxygen:nitrogen=0.99:4.6:14.1:0.49:79.8 in terms of percent by volume. WHSV was 0.030 $h^{-1}$, and SV was 600 $h^{-1}$. After 5.8 h from the initiation of the reaction, the reaction product gas flowing out of the top of the reaction tube was analyzed. The conversion of p-tolualdehyde was 99.7 mol %, the yield of p-tolunitrile was 97.2 mol %, and the selectivity was 97.5 mol %. The yield of by-produced terephthalonitrile was 0.97 mol %.

EXAMPLE 3

The procedure of Example 1 was repeated except for changing p-tolualdehyde to 4-ethylbenzaldehyde. The chemical composition of the mixed gas fed into the catalyst bed during the reaction was 4-ethylbenzaldehyde:benzene:ammonia:oxygen:nitrogen=1.1:5.4:2.8:0.56:90.2 in terms of percent by volume. WHSV was 0.032 $h^{-1}$, and SV was 531 $h^{-1}$. After 3.1 h from the initiation of the reaction, the reaction product gas flowing out of the top of the reaction tube was analyzed. The conversion of 4-ethylbenzaldehyde was 96.5 mol %, the yield of 4-ethylbenzonitrile was 88.0 mol %, and the selectivity was 91.2 mol %.

EXAMPLE 4

The procedure of Example 3 was repeated except for increasing the feeding amount of ammonia. The chemical composition of the mixed gas fed into the catalyst bed during the reaction was 4-ethylbenzaldehyde:benzene:ammonia:oxygen:nitrogen=1.0:4.8:14.2:0.49:79.5 in terms of percent by volume. WHSV was 0.034 $h^{-1}$, and SV was 602 $h^{-1}$. After 5.0 h from the initiation of the reaction, the reaction product gas flowing out of the top of the reaction tube was analyzed. The conversion of 4-ethylbenzaldehyde was 99.1 mol %, the yield of 4-ethylbenzonitrile was 94.8 mol %, and the selectivity was 95.7 mol %.

EXAMPLE 5

The procedure of Example 1 was repeated except for changing p-tolualdehyde to 4-isopropylbenzaldehyde. The chemical composition of the mixed gas fed into the catalyst bed during the reaction was 4-isopropylbenzaldehyde:benzene:ammonia:oxygen:nitrogen=1.0:5.9:3.3:0.55:89.1 in terms of percent by volume. WHSV was 0.035 $h^{-1}$, and SV was 537 $h^{-1}$. After 0.9 h from the initiation of the reaction, the reaction product gas flowing out of the top of the reaction tube was analyzed. The conversion of 4-isopropylbenzaldehyde was 97.9 mol %, the yield of 4-isopropylbenzonitrile was 87.2 mol %, and the selectivity was 89.0 mol %.

EXAMPLE 6

The procedure of Example 5 was repeated except for increasing the feeding amount of ammonia. The chemical composition of the mixed gas fed into the catalyst bed during the reaction was 4-isopropylbenzaldehyde:benzene:ammonia:oxygen:nitrogen=0.98:5.2:13.9:0.49:79.4 in terms of percent by volume. WHSV was 0.037 $h^{-1}$, and SV was 603 $h^{-1}$. After 5.0 h from the initiation of the reaction, the reaction product gas flowing out of the top of the reaction tube was analyzed. The conversion of 4-isopropylbenzaldehyde was 99.4 mol %, the yield of 4-isopropylbenzonitrile was 94.2 mol %, and the selectivity was 94.8 mol %.

EXAMPLE 7

The procedure of Example 1 was repeated except for changing p-tolualdehyde to 3,4-dimethylbenzaldehyde. The chemical composition of the mixed gas fed into the catalyst bed during the reaction was 3,4-dimethylbenzaldehyde:benzene:ammonia:oxygen:nitrogen=0.99:5.2:2.8:0.56:90.3 in terms of percent by volume. WHSV was 0.030 $h^{-1}$, and SV was 530 $h^{-1}$. After 1.0 h from the initiation of the reaction, the reaction product gas flowing out of the top of the reaction tube was analyzed. The conversion of 3,4-dimethylbenzaldehyde was 98.8 mol %, the yield of 3,4-dimethylbenzonitrile was 94.4 mol %, and the selectivity was 95.6 mol %.

EXAMPLE 8

The procedure of Example 7 was repeated except for increasing the feeding amount of ammonia. The chemical composition of the mixed gas fed into the catalyst bed during the reaction was 3,4-dimethylbenzaldehyde:benzene:ammonia:oxygen:nitrogen=1.0:5.0:14.1:0.49:79.4 in terms of percent by volume. WHSV was 0.035 $h^{-1}$, and SV was 603 $h^{-1}$. After 3.0 h from the initiation of the reaction, the reaction product gas flowing out of the top of the reaction tube was analyzed. The conversion of 3,4-dimethylbenzaldehyde was 99.7 mol %, the yield of 3,4-dimethylbenzonitrile was 96.9 mol %, and the selectivity was 97.2 mol %.

EXAMPLE 9

Reaction Using Regenerated Catalyst

In Example 1, after 6.8 h from the initiation of the reaction, the reaction product gas flowing out of the top of the reaction tube was analyzed. The conversion of p-tolualdehyde and the yield of p-tolunitrile were reduced to 95.0 mol % and 90.5 mol %, respectively. After 7.5 h from the initiation of the reaction, the feeding of the benzene solution of p-tolualdehyde and ammonia was discontinued. Then, the catalyst bed was calcined for 12 h by heating to 400° C. under an air/nitrogen mixed gas flow. The chemical composition of the air/nitrogen mixed gas fed into the catalyst bed during the calcination was oxygen:nitrogen=16.2:83.8 in terms of percent by volume. SV was 268 $h^{-1}$. Then, the reaction was repeated in the same conditions as used before the calcination of the catalyst. After 2.0 h from the initiation of the repeated reaction, the reaction product gas flowing out of the top of the reaction tube was analyzed. The conversion of p-tolualdehyde was 99.2 mol %, the yield of p-tolunitrile was 94.0 mol %, and the selectivity was 94.8 mol %.

EXAMPLE 10

Into a reaction tube having an inner diameter of 23 mmφ, 40 mL (42 g) of the catalyst obtained in Reference Example was packed. The temperature of the catalyst bed was raised to 320° C. (reaction temperature). A benzene solution containing 25% by weight of p-tolualdehyde, ammonia, air and nitrogen were introduced into an evaporating tube that had been heated to 320° C., and evaporated and mixed there before fed into the catalyst bed. Then the mixed gas was fed into the catalyst bed from its bottom to allow the fluidized catalytic reaction of the reactants to proceed. The chemical composition of the mixed gas fed into the catalyst bed during the reaction was p-tolualdehyde:benzene:ammonia:oxygen:nitrogen=1.0:4.8:3.0:0.56:90.6 in terms of percent by volume. WHSV was 0.027 $h^{-1}$, and SV was 528 $h^{-1}$. After 4.5 h from the initiation of the reaction, the reaction product gas flowing out of the top of the reaction tube was analyzed. The conversion of p-tolualdehyde was 99.97 mol %, the yield of p-tolunitrile was 78.3 mol %, and the selectivity was 78.3 mol %. The yield of by-produced terephthalonitrile was 1.6 mol %.

EXAMPLE 11

Into a reaction tube having an inner diameter of 23 mmφ, 40 mL (42 g) of the catalyst obtained in Reference Example was packed. The temperature of the catalyst bed was raised to 320° C. (reaction temperature). A benzene solution containing 25% by weight of p-tolualdehyde and nitrogen were introduced into an evaporating tube that had been heated to 320° C., evaporated and mixed there, and fed into the catalyst bed from its bottom. Simultaneously, ammonia and air that had been heated to 320° C. were fed into the catalyst bed at the position 5 mm above its bottom to allow the fluidized catalytic reaction of the reactants to proceed. The chemical composition of the mixed gas fed into the catalyst bed during the reaction was p-tolualdehyde:benzene:ammonia:oxygen:nitrogen=0.76:3.6:2.3:6.0:87.0 in terms of percent by volume. WHSV was 0.028 $h^{-1}$, and SV was 724 $h^{-1}$. After 1.8 h from the initiation of the reaction, the reaction product gas flowing out of the top of the reaction tube was analyzed. The conversion of p-tolualdehyde was 99.4 mol %, the yield of p-tolunitrile was 65.5 mol %, and the selectivity was 65.9 mol %. The yield of by-produced terephthalonitrile was 30.9 mol %.

The cyclic nitriles produced by the present invention are industrially useful compounds that are used as the intermediates for producing pigments, medicines, agricultural chemicals, perfumes, etc.

What is claimed is:

1. A method for producing an alkyl and/or cycloalkyl-substituted cyclic nitrile, which comprises a step of bringing a cyclic aldehyde having an alkyl group and/or a cycloalkyl group directly bonded to a skeletal ring and a formyl group directly bonded to the skeletal ring into contact with ammonia and oxygen in vapor phase in the presence of a catalyst to selectively ammoxidizing the formyl group into a cyano group, wherein the catalyst contains at least one oxide selected from the group consisting of oxides of V, Mo and Fe;

wherein the cyclic aldehyde is brought into contact with ammonia in an amount of 1 to 20 in terms of an equivalent ratio, ammonia/formyl group, with respect to the formyl group of the cyclic aldehyde; and wherein the cyclic aldehyde is brought into contact with oxygen in an amount of 0.4 to 50.0 in terms of an equivalent ratio, ($O_2$×2)/formyl group, with respect to the formyl group of the cyclic aldehyde.

2. The method according to claim 1, wherein a remaining ratio of the alkyl group and/or cycloalkyl group in the alkyl and/or cycloalkyl-substituted cyclic nitrile is 90 mol % or more of the alkyl group and/or cycloalkyl group in the cyclic aldehyde.

3. The method according to claim 1, wherein the cyclic aldehyde is fed into a reactor separately from ammonia and oxygen and bought into contact with ammonia and oxygen in the presence of the catalyst.

4. The method according to according to claim 1, wherein the catalyst further contains at least one oxide selected from the group consisting of oxides of Mg, Ca, Ba, La, Ti, Zr, Cr, W, Mn, Co, Ni, B, Al, Ge, Sn, Pb, P, Sb and Bi.

5. The method according to claim 1, wherein the catalyst further contains an alkali metal.

6. The method according to claim 1, wherein air is used as an oxygen source.

7. The method according to claim 1, wherein the catalyst deactivated by the reaction is reused after regeneration by calcination in the presence of oxygen.

8. The method according to claim 7, wherein a calcining temperature is 300 to 700° C.

9. The method according to claim 7, wherein an oxygen concentration of a calcination atmosphere is 1 to 21% by volume.

10. The method according to claim 7, wherein air is used as an oxygen source for the calcination.

* * * * *